United States Patent [19]

Santi

[11] Patent Number: 5,492,807
[45] Date of Patent: Feb. 20, 1996

[54] METHOD OF OBTAINING DIAGNOSTIC REAGENTS, ASSAYS AND THERAPEUTICS BASED ON CLINICAL MANIFESTATIONS OF A DISEASE

[76] Inventor: Daniel V. Santi, 211 Belgrave Ave., San Francisco, Calif. 94117

[21] Appl. No.: 155,943

[22] Filed: Nov. 19, 1993

[51] Int. Cl.[6] ............................................ C12Q 1/70
[52] U.S. Cl. ........................ 435/5; 435/6; 436/518; 436/811; 436/820
[58] Field of Search ........................... 435/5, 7.32, 7.22, 435/6; 436/506, 508, 518, 519, 545, 546, 800, 804, 811, 813, 820; 530/413, 806, 808; 935/82

[56] References Cited

U.S. PATENT DOCUMENTS

| | | | |
|---|---|---|---|
| 4,751,181 | 6/1988 | Keene | 435/70 |
| 5,010,175 | 4/1991 | Rutter et al. | 530/334 |
| 5,182,366 | 1/1993 | Huebner et al. | 530/334 |
| 5,223,409 | 6/1993 | Ladner et al. | 435/69.7 |
| 5,270,170 | 12/1993 | Schatz et al. | 435/7.37 |

FOREIGN PATENT DOCUMENTS

| | | |
|---|---|---|
| WO86/00991 | 2/1986 | WIPO. |
| WO86/06487 | 11/1986 | WIPO. |

OTHER PUBLICATIONS

Barbas, C. F., "Assembly of Combinatorial Antibody Libraries on Phage Surfaces: The Gene III Site" *Proc. Natl. Acad. Sci.* (1991) 88:7978–7982.

Brown, "Engineered Iron Oxide–Adhesion Mutants of the *Escherichia coli* Phage λ Receptor" *Proc. Natl. Acad. Sci. USA* (1992) 89:8651–8655.

Christian, R., et al., "Simplified Methods for Construction, Assessment and Rapid Screening of Peptide Libraries in Bacteriophage" *J. Mol. Biol.* (1992) 227:711–718.

Devlin, J. J., et al., "Random Peptide Libraries: A Source of Specific Protein Binding Molecules" *Science* (1990) 249:404–406.

Dybwad, A., et al., "Identification of New B Cell Epitopes in the Sera of Rheumatoid Arthritis Patients Using a Random Nanopeptide Phage Library" *Eur. J. Immunol.* (1993) 23:3189–3193.

Felici, F. "Selection of Antibody Ligands from a Large Library of Oligopeptides Expressed on a Multivalent Exposition Vector" *J. Mol. Biol.* (1991) 222:301–310.

Geysen, H .M. et al., "Use of Peptide Synthesis to Probe Viral Antigens for Epitopes to a Resolution of a Single Amino Acid" *Proc Natl Acad Sci USA* (1984) 81:3998–4002.

Houghten, R. A., "General Method for the Rapid solid–Phase Synthesis of Large Numbers of Peptides: Specificity of Anti–gen–Antibody Interaction at the Level of Individual Amino Acids", *Proc. Natl. Acad. Sci. USA*, (1985), 82:5131–5135.

Lam, K. et al., "A New Type of Synthetic Peptide Library for Identifying Ligand–Binding Activity" *Nature* (1991) 354:82–84.

Scott, J., et al., "Searching for Peptide Ligands with an Epitope Library" *Science* (1990)249:386–390.

Primary Examiner—Toni R. Scheiner
Assistant Examiner—Donna C. Wortman
Attorney, Agent, or Firm—Karl Bozicevic; Fish & Richardson

[57] ABSTRACT

Antibodies are recovered and isolated from the sera of a number "n" of patients each of which have or have had the same given disease so that each of the "n" patients has, within a large number of different antibodies, some antibodies uniquely associated with the same disease of interest. The antibodies of a first patient are bound to a support surface. To carry out initial screening libraries of molecules are brought into contact with the bound antibodies of the first patient under conditions where binding will occur. Secondary screening is then carried out by extracting and labeling the antibodies of a second patient and using the labeled antibodies to probe the molecules (peptides) isolated in the initial screening. Many of the non-disease specific antibodies (of the second patient) will not bind to the molecules (peptides) of the isolated bacteriophage which bound to the antibodies of the first patient. Hence, the molecules (peptides) which are common to both patients with the same disease will be identified. The process may be repeated with labeled antibodies from a third, fourth, etc. patient to obtain those molecules (peptides) which are common to all patients with the disease, and have the highest affinity to the antibodies specific to the disease. Copies of the characterized molecules (peptides) can be synthesized and bound to a support for use as an assay to detect the presence of antibodies specific to a disease.

20 Claims, No Drawings

METHOD OF OBTAINING DIAGNOSTIC REAGENTS, ASSAYS AND THERAPEUTICS BASED ON CLINICAL MANIFESTATIONS OF A DISEASE

FIELD OF THE INVENTION

This invention relates generally to the field of technology involved in the isolation, recovery, formulation and use of various compounds including peptides which selectively bind specific antibodies or other specific binding proteins that are characteristic of a disease state.

BACKGROUND OF THE INVENTION

The present invention is based, in part, on conventional knowledge of antibodies, the antigens which bind them, and known procedures for making large mixtures of peptides and other molecules which may bind to naturally occurring antibodies. Antibodies are proteins produced by lymphoid cells (plasma cells). The antibodies are produced by the cells in response to "foreign" substances (antigens), either exogenous or endogenous, and are capable of binding specifically with the antigen which stimulated the immune response. The antibodies can also bind with substances which are structurally similar to that same antigen. An antigen can be any foreign substance that, upon introduction into a vertebrate animal, stimulates the production of antibodies. An antigen may also be of endogenous source, such as antigens in auto-immune diseases or from tissue destruction. A complex antigen-like molecule may carry several antigenically distinct sites which are referred to as determinants. A substance which is structurally similar to certain parts of an immunogen (in general the determinants) can react specifically with its antibody. However, such smaller substances are generally too small to stimulate antibody synthesis by themselves and can be referred to as an incomplete antigen or hapten.

Throughout the life of vertebrate animals, such as humans, foreign substances are continually introduced. These foreign substances include viruses and bacteria which cause disease. Each time an antigenic substance is introduced it may result in the generation of a different antibody or several antibodies. Since many foreign substances are introduced over the life of the animal, and since many antibodies may be generated in response to a single foreign substance, each individual animal will have a large numbers of different antibodies. With present technology, it is very difficult to isolate and recover a specific antibody associated with a specific antigen or disease especially if nothing is known about the characteristics of the antibody or antigens involved. More specifically, if one or more individuals is known to have a given disease (wherein the agent responsible for the disease has not been characterized), it is not a simple matter to isolate the antibodies in that individual which have been generated and amplified as a result of that disease, nor is it a simple matter to isolate and recover antigens which bind to those antibodies. The present invention endeavors to provide approaches which make it possible to isolate and recover antibodies which are characteristic of a specific disease and to simultaneously isolate and recover antigens and/or related molecules which specifically bind to those antibodies.

In order to carry out the methodology of the present invention it is necessary to produce large numbers of peptides and/or other molecules which can be tested for their ability to bind to antibodies. These large mixtures of peptides and/or other molecules can be produced using technology described in the literature. One of the initial methods of producing multiple peptides more rapidly than the standard Merrifield method is disclosed by Houghten, R. A., Proc Natl Acad Sci USA (1985) 82:5131–5135. The Houghten method involves a modification of the Merrifield method but uses many individual polyethylene bags resulting in a method wherein each bag will contain a different peptide. An alternative method was devised by Geysen, H. M., et al., Proc Natl Acad Sci USA (1984) 81:3998–4002. (See also, WO86/06487 and WO86/00991). In accordance with the Geysen method, C-terminal amino acid residues are bound to solid supports in the form of multiple polyethylene pins and the pins treated in parallel to attach additional amino acid residues.

More recently, machines have been introduced which produce many peptides by parallel synthesis (e.g. Advanced Chem Tech, Gilson). An advancement in the ability to produce extremely large numbers of peptides as mixtures was disclosed within U.S. Pat. No. 5,010,175 issued Apr. 23, 1991 to Rutter and Santi. The Rutter and Santi method makes it possible to generate large numbers of peptides in either equimolar amounts or in predictable amounts. The methodology makes it possible to quickly synthesize large numbers of peptides such as mixtures containing 64 million or more different and distinct peptides. Another method for producing mixtures of peptides including large numbers of different peptides is disclosed within issued U.S. Pat. No. 5,182,366 issued Jan. 26, 1993 to Huebner et al. and in publications by Lam et al., Nature, (1991) 354, 82–84, and Prague paper.

The procedures described in the patents listed above allow for the production of peptides and/or modified peptides using chemical synthesis technology i.e. one compound is reacted with another in a chemical reaction in order to obtain a reaction product. Although these methods can be used in connection with the present invention, other recent technology involves the biological synthesis of peptides in large numbers. More specifically, the genetic material of bacteria or phage can be modified so that each bacterium or phage produce an individual peptide on their surface. By randomly producing large numbers of different pieces of altered genetic material it is possible to produce a mixture of bacteria or phage wherein the different bacteria or phage in the mixture include a different peptide expressed on the surface. One method of producing peptides on phage is taught by Devlin et al., Science (1990) 249:404–406 which discloses a method for the production and rapid evaluation of random libraries of millions of peptides on the surface of phage. A similar method was published by Scott and Smith, Science (1990) 249: 386–390. Scott and Smith disclose a method wherein peptides are produced on the surface of bacteriophage and the phage expressing a particular peptide tag can be selected from a mixture of tens of millions of clones expressing oligopeptides of random sequences using affinity purification with a protein ligand. Christian et al., J. Mol. Biol., (1992) 227:711–718 discloses simplified methods for the construction, assessment and rapid screening of peptide libraries in bacteriophage. Another related method involves the generation of libraries by insertion of peptides into the external domain of bacterial outer-membrane proteins, such as lam B, using recombinant technology Brown, Proc. Natl. Acad. Sci. USA (1992) 89: 8651–8655. Still another method of producing large numbers of peptides is taught in U.S. Pat. No. 5,223,409 issued Jun. 29, 1993 to Ladner et al.

All the above discussed methods for producing libraries of peptides and modified peptides can be used in connection with the present invention. Although the methods are extremely useful for producing large mixtures of peptides and modified peptides, the methodologies do not allow one to identify molecules which bind to antibodies in sera when neither the antibody nor the antigen is known, or to identify antibodies specific to a given disease. The present invention endeavors to provide technology which makes such possible.

SUMMARY OF THE INVENTION

The methodology of the present invention makes it possible to isolate peptides and/or other molecules which specifically bind to antibodies in sera which antibodies are specific to a given disease while simultaneously isolating those antibodies. In order to carry out the methodology, antibodies are isolated from the sera of a number "n" of patients, each with a history of having had the same given disease. The antibodies of a first patient are isolated and immobilized on a support surface in a manner which does not interfere with specific binding of antigens. To carry out the initial selection, libraries of peptides displayed on the surface of bacteriophage (or bacteria, or synthetic peptides on a solid support) are brought into contact with the immobilized antibodies of the first patient under conditions where binding will occur. (For descriptive purposes procedures using peptides displayed on phage are described below. However, similar approaches can be performed with bacteria, synthetic peptides, etc., by persons skilled in the art.). Unbound phage-peptides are washed away and antibody specific phage-peptides are removed, isolated, and recovered as plaques grown on a lawn of bacteria. Secondary screening is then carried out by isolating and labeling (radioisotopically or other method) the antibodies of a second patient and using the labeled antibodies to probe the peptides of the isolated bacteriophage binders identified in the initial selection (e.g. using methods similar to that described with pure monoclonal antibodies by Christian et al., J. Mol. Biol., (1992) 227:711–718 and Castagnoli et al., J. Mol. Biol. (1991) 222: 301–310. In that many of the antibodies of the first patient will differ from the antibodies of the second patient, many or most of the non-disease specific antibodies (of the second patient) will not bind to the peptides of the isolated bacteriophage which bound to the antibodies of the first patient. The peptides which are not bound by antibodies of the second patient are identified as not binding to antibodies of the disease of interest and are eliminated from the screening process. The process may be repeated with labeled antibodies from a third, fourth, etc. patient to obtain and identify those peptides having the highest affinity to the antibodies specific to the disease of interest. Those peptides found to have the greatest binding affinity are characterized—e.g. their amino acid sequences are determined by deducing such from the DNA sequences if the peptides are on phage or bacteria. The predicted peptides can then be chemically synthesized and bound to a support for use as a diagnostic assay to detect the presence of antibodies, or formulated in a pharmaceutical preparation which can be used to deactivate or neutralize antibodies in a living being.

A primary object of the invention is to provide a method for determining specific peptides which selectively bind to disease specific antibodies and isolating antibodies associated with a disease.

An important advantage of the present invention is that the methodology requires no prior knowledge of the molecular entities which cause a given disease or the antibodies which are generated by infection with the disease.

Another advantage of the present invention is that the isolated molecules which specifically bind to antibodies characteristic of a disease can be used to assay the sera of an individual for the presence of the disease and can, at times, be used to diagnose the progress of the disease within the individual by quantitative or qualitative differences in disease specific antibodies.

A feature of the invention is that the diagnostic reagents isolated, using the methodology of the present invention, are isolated and defined solely by the presence of common antibodies generated during a disease state of a number of individuals who have had or who are suffering from the disease. As such these antibodies define the disease by clinical description and are thus termed "disease-specific."

Another advantage and feature of the present invention is that the antibodies of a number of different patients (all with a given disease in common) are comparatively analyzed to eliminate non-common antibodies and thereby isolate common antibodies specific to a given disease of interest.

Another advantage of the invention is that very large numbers of peptides and other molecules can be quickly screened for their ability to bind to antibodies and thereafter isolated and characterized.

A feature of the invention is that it can be used in connection with libraries of synthetic peptides or cell surface peptides displayed on bacteriophage or bacteria.

Another object of the invention is to provide a diagnostic assay device comprised of a substrate having single or multiple antibody-binding peptides bound to the surface of the substrate.

Another advantage of the invention is that the methodology can be used to produce assays for a variety of different diseases which can be used to assay human and animal sera to determine the presence of antibodies associated with specific diseases and, perhaps associated with a specific state of a disease.

Another feature of the invention is that it is useful in developing not only assays but pharmaceutical formulations used in neutralizing the antibodies and thus, in some cases, the treatment of patients..

These and other objects, advantages and features of the present invention will become apparent to those persons skilled in the art upon reading the details of the methodology and usage as more fully set forth below.

DETAILED DESCRIPTION OF PREFERRED EMBODIMENTS

Before the present method of obtaining peptide diagnostic reagents, and assays and formulations using such are described, it is to be understood that this invention is not limited to the particular methodologies, assays and formulations described as such and may, of course, vary. It is also to be understood that the terminology used herein is for the purpose of describing particular embodiments only, and is not intended to be limiting since the scope of the present invention will be limited only by the appended claims.

It must be noted that as used in this specification and the appended claims, the singular "a", "and" and "the" include plural referents unless the context clearly dictates otherwise. Thus, for example, reference to "a peptide" includes mixtures of and large numbers of peptides, reference to "an antibody" includes large numbers of antibodies and reference to "the method of synthesis" includes one or more methods of synthesis known to those skilled in the art or understood by those skilled in the art upon reading the present application and so forth.

Unless defined otherwise all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference in order to describe and disclose the specific information for which the reference has been cited.

Definitions

The term "antibody" is defined in its broadest sense to encompass specific binding moieties, i.e., chemical moieties which specifically bind to other chemical moieties within a biological system. The term includes a protein molecule formed within the body of an animal in order to neutralize the effect of a foreign invading protein (called an antigen). The term further includes antibodies produced by lymphocytes in response to the presence of antigens wherein each antibody has a molecular structure that exactly fits the structure of one particular antigen molecule so that the antigen and antibody fit specifically to each other like a lock and key. The term encompasses antibody molecules which attach themselves to invading antigen molecules (which antigen molecules are generally on the surface of a pathogenic bacteria or virus) and thereby renders the bacteria or virus inactive.

The terms "peptide library" and "library of peptides" are used interchangeably herein. The terms are intended to encompass a mixture of peptides, preferably in the form of linear chains of amino acids containing four to 20 amino acids. A peptide library is intended to encompass mixtures which include 400 or more distinct and unique peptides, each present in the mixture in retrievable and analyzable amounts. Preferred mixtures include peptides which include the same number of amino acids e.g. mixtures containing only hexapeptides. A particularly preferred mixture includes peptides wherein each of the 20 naturally occurring amino acids is positioned at all possible positions in one of the peptides in the mixture. For example, a particularly preferred mixture of hexapeptides includes $20^6$ hexapeptides (64 million) with each of the 64 million hexapeptides being present in retrievable and analyzable amounts.

The term "peptide analog library" and "library of peptide analogs" are used interchangeably herein. The terms are intended to encompass a library of molecules which are preferably polymers and are preferably in the form of a linear chain of monomer units containing four to 20 monomer units. A peptide analog library includes large numbers of molecules such as defined above with respect to a "peptide library." Peptide analogs include peptides which incorporate Doamino acids, amino acid analogs and other organic molecules which can be linked together as monomer units in order to form a polymer.

The term "disease specific antibody" (DSA) is intended to encompass any antibody produced by a living being having an immune system which is uniquely associated with a given disease and, as such, is an antibody or antibodies specifically generated as a direct or indirect result of the disease.

The term "non-disease specific antibody" (NDSA) is intended to encompass all antibodies in an organism other than the disease specific antibodies. Non-disease specific antibodies may have been generated as the result of a wide range of different antigenic materials including prior diseases which are not the specific disease of interest.

The term "antibody-binding peptides" is intended to encompass linear peptides (preferably containing four to 20 amino acids) which will bind to an antibody under conventional antibody/antigen binding conditions. Preferred antibody-binding peptides are linear peptides which selectively bind to disease specific antibodies and which do not bind to non-disease specific antibodies.

The term "antibody-binding molecule" is intended to encompass antibody-binding peptides and other molecules such as peptide analogs or organic molecules which selectively bind to an antibody under conventional antibody-antigen binding conditions. Preferred antibody-binding molecules are linear polymeric molecules or organic molecules containing four or more monomer units which selectively bind to disease specific antibodies and which do not bind, or bind less tightly, to non-disease specific antibodies.

General Methodology

The methodology of the present invention makes it possible to isolate molecules, such as peptides, which selectively bind to the disease specific antibodies with no prior knowledge of the immune response and subsequently to isolate and identify these antibody molecules. Having isolated antibody-binding molecules such as peptides they can be chemically synthesized and used in assays or formulated for use as therapeutics. Having isolated and recovered pure antibodies they might in some cases be sequenced and copies can be produced.

The methodology is carried out by extracting the antibodies from sera from a number of patients all of whom have the same disease of interest but who are otherwise immunologically heterogeneous. The antibodies from different patients are compared to ascertain which antibodies are the disease specific antibodies (DSA) common to patients who have the disease of interest. The antibody-binding peptides or other molecules of interest can then be identified using the DSA. Thereafter, the antibody-binding molecules can be used in assays to determine the presence of disease specific antibodies within the sera of other patients being tested, or can be formulated for use as therapeutics.

The "Background of the Invention" section put forth above describes a number of methodologies for producing peptide libraries and/or peptide analog libraries. Any of these methodologies and others can be used in connection with the general methodology of the present invention. In general, chemical synthesis methodologies such as disclosed within U.S. Pat. No. 5,010,175 to Rutter and Santi or Huber and Santi, or Lam et al., can be used to produce large libraries of peptides synthetically. The amino acid monomer units can be modified so that this technology can be used to produce peptide analog libraries synthetically. Alternatively, methods such as disclosed within the above cited Devlin et al. and Scott and Smith articles can be used to produce large libraries of peptides expressed on the surface of bacteriophage. Alternately, organic-diversity libraries as described (Pauwels, et al. Proc. Natl. Acad. Sci. USA (1993) 90: 1711–1715; Bunin, B. A. and Ellman, J. A. (1992) 114, 10997–10998; DeWitt, S. H. et al., (1993) 90: 6909–6913) might be used to identify novel organic-molecule diagnostic reagents. Although any of these methods can be used it is, of course, necessary to use chemical synthesis methodology if the antibody binding molecules are different from peptides. More specifically, chemical synthesis methodology must be used to produce peptide analogs and related organic compounds which might bind antigens. However, for purposes of simplicity and efficiency it is preferable to use peptide libraries where the peptides are produced on the surface of bacteriophage or bacteria in accordance with the nonproprietary methods described in Devlin et al., Science (1990) 249: 404–406; Scott and Smith, Science (1990) 249: 386–390; Christian et al., J. Mol. Biol., (1992) 227: 711–718; Castagnoli et al., J. Mol. Biol. (1991) 222: 301–310 and Brown, Proc. Natl. Acad. Sci. USA (1992) 89: 8651–8655. For this reason, the following specific description refers to the use of a peptide library produced on bacteriophage. However, it should be noted that, having read the present disclosure, those skilled in the art could readily modify the following description so that the methodology could be carried out using various libraries including libraries on the surface of bacteria, synthetic peptide analog libraries and libraries of organic compounds produced using chemical synthesis technology.

Initial Sera/Antibody Cleanup

To carry out the methodology of the invention the sera of a number "n" of patients (e.g. 10 patients), each diagnosed with the same disease of interest, are extracted. It is critical that each of the patients be definitively diagnosed as having the disease of interest. It is desirable that the patients are otherwise different with respect to their immunological background so that most antibodies in common are disease specific. This could be accomplished, to a certain extent, by choosing patients of diverse genetic backgrounds and from diverse locations around the world.

Having extracted the sera from the different patients, the serum from each of the patients is subjected to an initial cleanup procedure which involves the removal of interfering substances in order to simplify the search for the antibodies of interest. For example, the sera are brought into contact with the proteins of *E. coli,* and the antibodies which specifically bind to the *E. coli* proteins (due to previous exposures) are removed. Other common high titer antibodies can also be removed from the sera in an analogous fashion. Techniques for carrying out such cleanup procedures involve contacting the antibodies with *E. coli* K-12 lysate using procedures such as those described in laboratory handbooks such as Sambrook, Fritsch and Maniatis (1989), Cold Spring Harbor Laboratory Press. The antibodies are then purified by column separation techniques such as a protein A column in order to isolate IgG antibodies. The isolated antibodies can then be subjected to elimination methodology in an attempt to remove as many non-disease specific antibodies as possible.

The serum extracted from each of the "n" patients is subjected to the initial antibody extraction and cleanup procedures of the type described above. Having done so, one will obtain individual pools of antibodies (e.g. 10 pools of antibodies from 10 individuals) which include the disease specific antibodies from each of the 10 individuals along with large numbers of non-disease specific antibodies. It is these 10 pools which are to be comparatively sorted per the present invention, one against the other, in order to discern the disease specific antibodies common to all of the 10 pools. Any antibodies common to all 10 pools is almost certainly a disease specific antibody and the present invention is directed towards obtaining such disease specific antibodies.

It should be pointed out that the broadest possible interpretation of the present invention would not require the use of the initial clean-up procedure. In accordance with the broadest interpretation of the present invention, the antibodies of a first patient would be comparatively sorted against the antibodies of a second patient. If the first and second patient did not share any antibodies except for the disease specific antibodies of interest, antibody-binding molecules could be readily identified along with the binding antibodies. However, in practice the use of the initial clean-up procedure could be important in reducing the number of antibodies which would need to be subjected to further comparative sorting per the present invention.

A variety of initial antibody clean-up procedures can be used. Those skilled in the art will recognize that different procedures might be more useful in connection with the treatment of the sera from particular populations than would other techniques. For example, patients from a given population may be very likely to have generated antibodies with respect to a given disease, whereas patients from another population would be very unlikely to have generated antibodies specific to that disease. For example, malaria is more common in some populations than in others. Accordingly it might be more efficient to screen out malaria specific antibodies from some populations routinely whereas screening for such antibodies in a patient population unlikely to have been infected with malaria would not be efficient.

The initial clean-up procedure described above does not require the use of any peptide library or peptide analog library and thus can be carried out in the same manner regardless of what type of library is being used for subsequent screening. However, with respect to the next section referred to as "Initial Selection" it is necessary to generate some type of library. As indicated above, for purposes of simplicity, the methodology is described with respect to the use of a peptide library and specifically a peptide library which has been generated on the surface of bacteriophage as described in the Scott and Smith, 1990, article cited above. However, all types of libraries (including organic compounds which are not peptides, but which mimic peptide or other molecules (e.g. carbohydrates, nucleic acids, etc.) in their ability to bind antibodies) could be used in the methodology of the present invention.

Initial Selection

Even after the initial extraction and cleanup procedures it would be expected that each of the 10 pools of extracted antibodies would include a number of disease specific antibodies and disease non-specific antibodies, e.g. 10 disease specific antibodies mixed with a much larger number of non-disease specific antibodies, e.g. 1,000 non-disease specific antibodies. As indicated, the numbers used here are chosen merely for example. The exact number of disease specific antibodies and non-disease specific antibodies present in each pool are unknown, and will vary based on a number of factors such as the disease and the individual from whom the antibodies were extracted. However, in general, each pool will include several antibodies specific to the disease and a much larger number of antibodies which are not specific to the disease. The fact that a small number of disease-specific antibodies are hidden within a much larger number of non-disease-specific antibodies is a natural phenomenon which emphasizes the importance of the present invention. More specifically, the methodology of the present invention makes it possible to select out the disease-specific antibodies from among a much larger number of non-disease-specific antibodies.

A pool of antibodies from a first patient (patient A) are immobilized to a given support surface. The antibodies are bound in a manner so as to not hinder binding of antigens to them. A library of peptides (phage, bacteria, synthetic peptides, or other molecules) is then brought into contact with the immobilized antibodies bound to the support surface. The library of peptides is preferably created on the surface of bacteriophage wherein each of the phage will express a different peptide, e.g., a hexapeptide. Such a phage library can be produced in accordance with procedures known to those skilled in the art e.g. as described in the references cited above. In essence, the procedures involve the random synthesis of nucleotides which will encode 64 or more million hexapeptides and randomly inserting the oligonucleotides into the genome of bacteriophage. It is preferable to use a peptide library created on the surface of bacteriophage in that any given peptide in the library which is found to be of interest can be readily purified by plaque purification and amplified by using the bacteriophage to infect bacteria and undergo replication.

The peptide library on the bacteriophage is brought into contact with the immobilized antibodies from patient A which were bound to a support. In order to reduce the background of non-disease-specific antibodies, an excess of blocking antibodies from disease-free individuals may be added to the bacteriophage library in advance and/or simultaneously co-incubated. Conventional antibody/peptide binding conditions can be used. After sufficient time has been allotted for the binding of the peptides (on the bacteriophage) to the immobilized antibodies bound to the support, conventional procedures are utilized to wash unbound peptides (bacteriophage) and bacteriophage-"blocking antibody" complexes from the area leaving only those peptides (bacteriophage) which bind to the immobilized antibodies.

The antibody-binding peptides (phage) are then removed and isolated. The isolated peptides (phage) can be used to infect bacteria and create unique, purified plaques of the bacteriophage. At this point, the initial selection step of the present invention has been completed. Specifically, a library of molecules has been generated and those molecules have been demonstrated to bind to the antibodies from a first patient. At this point, the "initial selection" step of the invention has been completed. However, the initial selection step can be further elaborated on in order to determine which of the antibody-binding peptides bind most strongly to the antibodies of the first patient. This procedure is described below.

Initial Selection (Increased Binding Affinity)

Copies of the antibody-binding peptides can be brought into contact with the antibodies from patient A bound to a support in order to determine which of the peptides bind to the antibodies with greatest affinity. The binding conditions can be changed (such as to make conditions for binding more difficult) in order to determine those antibody binding peptides which have the highest affinity for the antibodies. Although the procedures need not be repeated, it can be repeated any number of times and can be used to identify not only peptides which have higher affinity for antibodies but used to deduce which antibodies are present in high titer and therefore more likely to be related to the specific disease of interest.

Secondary Screening—Identifying Overlapping Epitopes in Different Sera

To a large extent the present invention is characterized by the secondary subsequent screening step. In the second step antibodies which have been isolated and subjected to initial "cleanup" procedures from a second patient (patient B) are labeled with an appropriate detectable label such as biotin, fluorescein or appropriate radioactivity. The labeled antibodies of patient B are then used as probes by bringing the labeled antibodies into contact with the bacteriophage colonies created by the antibody-binding peptides from patient A. In one method, the antibody-binding peptides are bound to a membrane and plaque hybridization procedures are used Christian et al., J. Mol. Biol., (1992) 227: 711–718.

A representative sample of phage are used to infect male *E. coli* (phage:*E. coli*::1:100). Approximately 50,000 colonies are plated on Luria broth (LB) plates with tetracycline (20 µg/ml; 1000 colonies/plate) and incubated overnight at 37° C. Phage are transferred to nitrocellulose filters by simple overlay. The filters are immediately washed twice (30 minutes/wash) with TNT buffer (10 mMTris-HCl, pH 8.0, 150 nM NaCl, 0.05% Tween 20) and soaked for 30 minutes at room temperature in a blocking solution containing 20% IgG from individuals who do not have the disease of interest to help block non-disease-specific interactions.

The filters are then incubated for two hours at room temperature in a 1:1000 dilution of the biotinylated IgG preparation from patient B in the above blocking solution (15 ml/filter). The filters are washed three times at room temperature: first with TNT, 0.1% albumin for 10 minutes; second with TNT, 0.1% albumin, 0.1% Nonidet P-40; and finally again in TNT, 0.1% albumin. An avidin-horseradish peroxidase (HRP) conjugate (Boeringer-Mannheim) is diluted 1:200 (v/v) in blocking solution (above) and incubated with the filters for two hours at room temperature (15 ml/filter). The filters are again washed three times as described above. Reactive clones are then identified by color development using 3,3' diaminobenzidine tetrahydrochloride as directed by the manufacturer (Pierce).

Many of the labeled antibodies of patient B will not bind to the same antigens (phage colonies/plaques) to which the antibodies of patient A bound. These antibodies will be assumed as non-disease specific antibodies of patient B and can be ignored. That is, any of the plaques or colonies isolated using antibodies from patient A which do not have a patient B labeled antibody bound thereto can be assumed as false positives or peptides which are not specific to the disease of interest (i.e. peptides which do not bind to antibodies emanating from the disease of interest). Since many or most of the non-disease-specific antibodies will differ between patients A and B this secondary screening procedure makes it possible to eliminate a large number or, in an unusual situation, all of the non-disease specific antibodies. Most importantly, it will identify those antibodies or antibody-binding peptides which are common to the patients with the disease.

At this point, it is possible (although not likely) to isolate specific peptides which specifically bind to only disease-specific antibodies. Such peptides could be chemically synthesized and tested in order to determine if they do selectively bind to disease-specific antibodies in high affinity. If positive results were obtained no further steps would be necessary other than to bind the antibody-binding peptides to a support for use as an assay and/or formulate the peptides for use as a therapeutic (e.g., a vaccine or blocking agent which blocks the effects of the antibodies of autoimmune diseases). More likely, further steps will be generally required in that any two given patients are likely to share more common antibodies than those generated in response to the disease of interest.

In that a single secondary screening step is unlikely to give the final desired results the procedure carried out with the antibodies from patient B are then repeated with the antibodies in sera of patient C. More specifically, the antibodies which were extracted and subjected to initial "cleanup" procedures from a third patient (patient C) are labeled in a similar manner as the antibodies of patient B were labeled. These labeled antibodies of patient C are brought into contact with at least the peptides which bound to antibodies of patients A and B. In practice, the labeled antibodies of patient C will be contacted with the same plaque pattern as was used with patient B. When binding occurs with the labeled antibodies from patient C it is matched to the plaques where binding occurred with the labeled antibodies of patients A and B. Any matching in antibody binding between patients A, B and C is seen as a potential positive. However, any non-common binding is an indication of a false positive. More specifically, if binding occurs to the peptides of patient A using labeled antibodies from patient B but does not occur using labeled antibodies from patient C (or vice versa) a false positive can be deduced, i.e., it can be deduced that these peptides and antibodies are not specific to the disease of interest. This is true in that all patients have been diagnosed as having the same specific disease of interest and therefore should share some antibodies which bind a common antigen associated with the disease.

The procedure carried out with the antibodies of patients B and C can again be repeated with a fourth patient (patient D). The procedures are essentially repeated with the antibodies from "n" patients until it is possible to determine that the remaining antibody or antibodies as well as the remaining peptide or peptides to which they bind are specific to the disease and are not non-disease-specific antibodies. A schematic diagram showing a comparison of the results which can be obtained using the labeled antibodies of patients B, C and D is shown below:

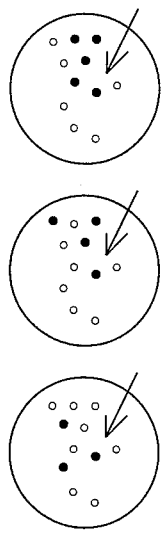

As can be seen in the diagram shown above, the labeled antibodies of patient B are indicated by the black plaques. When the antibodies of patient C are tested against the same plaque pattern there is an overlap of three plaques which can be identified as potential disease-specific antibodies. When the procedure is repeated with the labeled antibodies of patient D only one of the plaques is shown to be common to all the patients. In that the antibodies of patients A, B, C and D all bind to the peptide of a single plaque (which includes a single peptide) that peptide can be identified as one which binds to an antibody specifically associated with the disease of interest.

When secondary screening steps (with labelled antibodies of patients B, C, D, etc.) have been repeated with a sufficient number of patients, it will be possible to simultaneously identify peptide-binding molecules which bind to disease-specific antibodies characteristic of the disease of interest, i.e., determine antibodies and antigens of interest. The peptide-binding molecules such as peptides on a bacteriophage are then recovered and sequenced. If the peptide is generated on the surface of a bacteriophage it is more convenient to sequence the DNA and thereby deduce the amino acid sequence of the peptide. Having done this the peptide or peptides of interest can be chemically synthesized in greater amounts. The peptide or peptides can then be tested against the sera of other patients diagnosed with the disease in order to determine if they specifically bind to antibodies common to all patients suffering from the disease of interest.

Methods of Use

Chemical synthesis technology of the type described in the Background of the Invention can be used to produce large numbers of peptides which have been identified as specifically binding to antibodies which are specific to the disease of interest. In general, such peptides are useful in the production of an assay which can diagnose the presence of the disease of interest. Specifically, one or more such peptides are bound to a support surface and the sera of a patient being tested is brought into contact with the bound peptides. Since only antibodies which are specific to the disease of interest will bind to these peptides, binding to the peptides is an indication of the presence of the disease of interest. In most situations, the above-described procedure will identify a large number of distinct and different molecules including different peptides which will be useful in diagnosing a given disease. Hence, the invention will provide a multiple-reagent diagnostic capable of providing sensitivity not previously possible. Further, negative control peptides are obtained in the same procedure.

Some peptides found to bind to the antibodies of the disease of interest will be useful in the form of preventative or therapeutic formulations. More specifically, the peptides can be combined with pharmaceutically acceptable excipients and administered by injection in order to generate antibodies and thereby act as a vaccine (see, Keller et al., Virology (1993) 193: 709–716). However, it is pointed out that smaller peptides are often incapable of generating an antibody response or are incapable of generating an antibody response which will be effective in preventing infection with the disease; this could be overcome by conjugating the peptide to an immunologically inert carrier. Moreover, such formulations may also be useful in that they will bind to and block antibodies associated with an undesirable condition, e.g. an auto immune disease.

The present invention also makes it possible to isolate antibodies which are specific to a disease. Once isolated, the antibodies can be sequenced and reproduced. Such antibodies could also be used in assays and/or therapeutically. In certain instances, such may not be practical in that it is substantially more complex to reproduce the antibodies than it is to reproduce the peptides and/or other molecules which bind to these antibodies. However, the antibodies isolated by the above procedure can be put to practical use. More specifically, the antibodies can be bound to a support and used to screen libraries of peptide analogs and/or a wide range of organic compounds to determine whether those compounds selectively bind to the antibodies. When molecules which selectively bind to these peptides are isolated and recovered they can be reproduced, and used in assays and/or as therapeutics in the manner described above.

EXAMPLES

The following examples are put forth so as to provide those of ordinary skill in the art with a complete disclosure and description of how to carry out the methodology and produce and assays and formulations of the present invention and use such and are not intended to limit the scope of what the inventors regard as their invention. Efforts have been made to ensure accuracy with respect to numbers used (e.g., amounts, temperature, pH, etc.) but some experimental errors and deviations should be accounted for. Unless indicated otherwise, parts or parts by weight, molecular weight is a weight average molecular weight, temperature (18°–25° C.) is in degrees centigrade and can be assumed at room temperature, and pressure is assumed at or near atmospheric.

Before describing the Examples, the following information is provided regarding specific procedures, conditions, reagents, etc.

Condition for Antibody Isolation-clean-up

An extract is generated by freezing and thawing several times a suspension of $E.$ $coli$ in a simple lysis buffer (50 mM tris, pH 8.0, 10 mM EDTA). This extract is cleared by centrifugation at 12,000 g for 10 minutes to produce a lysate. The sera to be cleared is diluted 1:10 with TNT buffer (as described below) and mixed with lysate (0.5 ml lysate for every ml of diluted sera). The mixture is incubated for 4 hours at room temperature and subsequently cleared by high speed centrifugation (Sambrook et al. 1989). A similar procedure can be performed substituting a concentrated preparation of M13 mp18 (1014 pfu/ml) for the $E.$ $coli$ lysate.

Creating Colonies(Plaques)

A representative sample of phage are mixed together with an excess of male $E.$ $coli$, such as strain K91 (phage:$E.$ $coli$::1:100) in sterile Luria broth at 37° C. for 15–30 minutes to allow infection and expression of relevant markers (appropriate inducing agents having been added to the broth if necessary). Aliquots are plated on Luria broth (LB) plates with antibiotics or selective agents and incubated overnight at 37° C.

Peptide/Antibody Binding Conditions

The IgG or sera preparations are biotinylated using biotin-XX-NHS (Calbiochem) as described by Parmley and Smith (1988). Fifty µl of this preparation (7.5 µg of IgG) is incubated with streptavidin coated oxirane beads (10 mg, 10 nmol/gram resin) for one hour at room temperature with gentle agitation (final IgG concentration 1.0 µM). The beads are washed with phosphate buffered saline (PBS), 0.1% albumin to remove unbound IgG. 1011 transducing units (1012/ml) of a phage library are incubated with the phage at room temperature for two hours with gentle agitation. The unbound phage are removed by washing several times, i.e., re-suspending the beads in PBS, 0.5% Tween 20, briefly centrifuging to pellet the beads and removing the supernatant. The specifically bound phage are eluted using 400 µl of 0.1M glycine pH 2.22 as described (Christian et al., J. Mol. Biol., (1992) 227: 711–718).

EXAMPLE 1

This example is designed specifically to simulate an in vivo situation. The IgG fraction from four different rabbit sera is purified using Protein A columns as described by the manufacturer (Pierce). The four IgG fractions are pre-cleared twice with an excess of $E.$ $coli$ K-12 lysate, and twice with a 100 fold excess of M13 mp18 using materials and procedures of the type described by Sambrook, et al. (1989). The resulting fractions are divided in two and one portion spiked with a purified mouse monoclonal antibody (0.05% w/w). The other portion is left unspiked as a negative control. The four spiked IgG preparations are biotinylated using biotin-XX-NHS (Calbiochem) as described by Parmley and Smith (1988).

Two rounds of affinity selection are performed as described in Christian, R. B., et al., J Mol Biol (1992) 227:711–718 using the spiked IgG preparation from rabbit number 1 in place of the monoclonal antibody. Fifty µl of this preparation (7.5 µg of IgG) is incubated with streptavidin coated oxirane beads (10 mg, 10 nmol/gram resin) for one hour at room temperature with gentle agitation (final IgG concentration 1.0 µM). The beads are washed with phosphate buffered saline (PBS), 0.1% albumin to remove unbound IgG. 1011 transducing units (1012/ml) of a fuse 5-based phage library with amino acid inserts (Scott and Smith, Science (1990) 249: 386–390) are incubated with the phage at room temperature for two hours with gentle agitation. The unbound phage are removed by washing several times, i.e., re-suspending the beads in PBS, 0.5% Tween 20, briefly centrifuging to pellet the beads and removing the supernatant. The specifically bound phage are eluted using 400 µl of 0.1M glycine pH 2.22 as described (Christian et al., J. Mol. Biol., (1992) 227: 711–718).

The eluted phage are neutralized with 60 µl of 1M Tris-HCl pH 9.0, amplified and repanned under more stringent/competitive conditions (Christian et al., 1992). 1011 transducing units (1012/ml) are incubated directly with the biotinylated IgG fraction from rabbit number 1 (750 ng; 250 nM final concentration) for 2 hours at room temperature. The bound complexes are removed from solution by adsorption for 30 minutes at room temperature to a streptavidin coated plastic petri plate (Scott et al., 1990). Unbound phage are removed by washing the petri plate extensively (8 times) with PBS, 0.5% Tween 20 (7 ml/wash). The bound phage are eluted and neutralized as described above.

A representative sample of these phage are used to infect $E.$ $coli$, strain K91 (phage:$E.$ $coli$::1: 100). Approximately 50,000 colonies are plated on Luria broth (LB) plates with tetracycline (20 µg/ml; 1000 colonies/plate) and incubated overnight at 37° C. Phage are transferred to nitrocellulose filters by simple overlay (Christian et al., 1992). The filters are immediately washed twice (30 minutes/wash) with TNT buffer (10 mM Tris-HCl, pH 8.0, 150 nM NaCl, 0.05% Tween 20) and soaked for 30 minutes at room temperature in a blocking solution containing 20% unspiked (unbiotinylated) rabbit IgG preparation from rabbit 1 in TNT buffer.

The filters are then incubated for two hours at room temperature in a 1:1000 dilution of the spiked and biotinylated IgG preparation from rabbit number 2 in the above blocking solution (15 ml/filter). The filters are washed three times at room temperature: first with TNT, 0.1% albumin for 10 minutes; second with TNT, 0.1% albumin, 0.1% Nonidet P-40; and finally again in TNT, 0.1% albumin. The secondary antibody, goat anti-mouse IgG-horseradish peroxidase (HRP) conjugate (Boeringer-Mannheim) is diluted 1:200 (v/v) in blocking solution (above) and incubated with the filters for two hours at room temperature (15 ml/filter). The filters are again washed three times as described above. Monoclonal reactive clones are then identified by color development using 3,3' diaminobenzidine tetrahydrochloride as directed by the manufacturer (Pierce).

For comparison, filters are stripped (Sambrook et al., 1989) and reprobed a second time exactly as described above; however, the secondary antibody is replaced with an equivalent dilution of an avidin-HRP conjugate (Boeringer-Mannheim). This is to help assess the number of clones that cross-react between the IgG preparations from rabbit 1 and 2 (other than the mouse monoclonal). To extend this analysis and test the practicality of multiple reprobings, the filters are stripped and probed twice more: once with the spiked biotinylated IgG preparation from rabbit 3 (followed by the avidin-HRP conjugate) and finally with the preparation from rabbit 4.

EXAMPLE 2

The general strategy in Example 1 is also applicable to chemically synthesized libraries. The primary advantage of using such libraries is that molecules other than L amino acids can be incorporated, screened and identified for use as diagnostics and therapeutics. Chemically synthesized libraries can incorporate both D and L amino acids, β-amino acids and amino acids with unusual side-chains such as adamantyl groups. Furthermore this strategy allows the screening of peptide-like polymers such as peptoids, poly-ureas, etc. and libraries of organic molecules.

To perform the above and the following experiments with a peptide, peptide-like or organic library on beads (Lam et al., Nature, (1991) 354, 82–84) the beads are handled in a fashion analogous to that of the nitrocellulose filters above. Beads are washed and blocked as described for the in situ hybridization of the filters, probed with the biotinylated IgG preparations and after washing developed with the appropriate HRP conjugate and 3,3' diaminobenzidine tetrahydrochloride using appropriately reduced volumes of all solutions. To further facilitate visual identification of reactive beads during repeated screenings, the beads may be immobilized into porous polymer sheets. Processing of these sheets is identical to that of the nitrocellulose filters.

EXAMPLE 3

The feasibility of the methodology described above in Example 2 can be readily demonstrated by using rabbit sera containing anti-peptide antibodies. The use of such can demonstrate that polyclonal antibodies can be used in such experiments. Rabbit anti-peptide sera can be produced against a specific peptide and tested against a peptide library containing the peptide sequence.

The methodology can be carried out using four rabbits immunized with the peptide antigen coupled to KLH. Pre-immune serum is obtained for all four rabbits, IgG purified and preadsorbed with E. coli lysates and M13 mp18 phage as described above. Post-immunization serum is processed in an identical fashion and in addition is biotinylated.

Two rounds of affinity purification are performed using the biotinylated IgG preparation from rabbit 1. Phage obtained after the second round are plated and grown overnight on LB plates with tetracycline as described above. Filters are generated, blocked with 20% pre-immune IgG (unbiotinylated) from rabbit 1 and probed with a 1:200 dilution of the post-immunization IgG (biotinylated) from rabbit 2 in blocking solution. Cross-reacting clones are identified using avidin-HRP conjugates and 3,3' diaminobenzidine tetrahydrochloride as described above. Filters are then stripped and reprobed in separate experiments with the post-immunization IgG from rabbits 3 and 4.

Colonies found to cross-react with post-immunization IgG from rabbits 2, 3 and 4 are re-plated, transferred again to filters, blocked with re-immune IgG from rabbit 1 and reprobed with an equimolar mixture of pre-immune IgG from rabbits 2, 3 and 4 that has been biotinylated in order to rule out possible artifactual cross-reactivity. Post-immunization reactive colonies that are not reactive with pre-immune IgG are isolated and grown in Luria broth with tetracycline (20 µg/ml) and the recovered phage sequenced using Sanger dideoxy methods. Amino acid sequences deduced from these data are then used to generate synthetic peptides which are assayed by ELISA techniques to obtain binding constants as described (Christian et al., J. Mol. Biol., (1992) 227: 711–718).

In order to carry out the invention with human sera, it is necessary to ascertain the efficacy of blocking filters with IgG preparations from other individuals (i.e., cross-blocking). Fresh lifts are prepared from the plates of the original experiment (i.e., the plates generated with the phage eluted from the second round of panning with the post-immunization IgG from rabbit 1); however this time they are blocked with an equimolar mixture of pre-immune IgG from rabbits 3 and 4 (i.e., 10% of pre-immune IgG from rabbit 3 and rabbit 4 in TNT buffer). The filters are again probed with post-immunization IgG from rabbit 2 followed by avidin-HRP conjugate and the results compared with those obtained in the previous experiment.

EXAMPLE 4

The general methodology and materials described above in Examples 1–3 for identifying peptides or small molecules that react with DSA's can be tested using human sera from individuals with diseases such as Hepatitis C (HCV). An example of how such procedures are applied is described further below.

Samples of sera are obtained from several patients with confirmed hepatitis C (HCV). In addition sera from several healthy individuals of corresponding HLA type are obtained. As in the previous experiments, IgG fractions are prepared from all sera and pre-cleared with both E. coli lysates and M13 mp18. IgG preparations from HCV patients are biotinylated as before.

The biotinylated IgG preparation from HCV patient number 1 is used for two rounds of affinity enrichment as described above. The phage obtained following round 2 are plated (>100,000 colonies) and transferred to nitrocellulose filters. Filters are washed and subsequently blocked with 20% IgG (unbiotinylated) in TNT, pooled from the healthy individuals. Filters are probed with the biotinylated IgG from all of the other HCV patients individually by stripping and reprobing the filter set as described above. Finally the filters are probed with the pooled IgG preparation from the healthy individuals (biotinylated) to check for non-specific cross-reactivity and determine the percentage of the panned phage which react with typical human IgG. Clones reactive with all HCV patient IgG preparations but unreactive with the pooled IgG from healthy individuals are isolated, grown and the phage sequenced. Synthetic peptides are then generated and binding constants determined.

EXAMPLE 5

Feasibility of producing therapeutic peptides which inhibit a toxic antibody effect. In hemolytic disease of the newborn, maternal antibodies are produced which are directed against the Rh(D) antigen on fetal erythrocytes. These antibodies cross the placenta and destroy fetal red blood cells, resulting in significant fetal morbidity and in severe cases, fetal death. The only treatment is intrauterine fetal transfusions, an expensive procedure with significant associated morbidity. A novel therapy would be to develop ligands which bind to the antigen binding site and block binding of the antibodies to erythrocytes. This may be particularly possible for Rh(D) because the Rh(D) polypeptide chain is highly integrated in the cell membrane with very short extracellular domains which may well act as linear epitopes (Agre, P. and Cartron, J. Blood (1991) 78: 551–563). In addition the variable region gene usage of anti-D antibodies is structurally restricted suggesting that a ligand which binds to one anti-D antibody may also bind to many others (Bye, et al. J. Clin. Invest. (1992) 90: 2481–2490).

Samples of sera are obtained from a number of Rh(D) negative donors who have been immunized with the Rh(D) positive erythrocytes and who have been shown to be producing anti-Rh(D) antibodies. These could be either pregnant women or volunteer donors who are immunized for the production of commercial anti-D. IgG fractions are prepared as described previously, pre-cleared with *E. coli* lysates and M13 mp18, and biotinylated. The biotinylated IgG preparations from donor 1 is used for two rounds of affinity enrichment as described previously. Eluted phage from the second round of selection are used to infect *E. coli* and the bacteria plated on LB plates. Colonies are transferred to nitrocellulose and blocked with unbiotinylated 20% IgG in TNT from healthy individuals without detectable levels of anti-D. Filters are probed with biotinylated IgG from all the other anti-D producing donors. Clones reactive with anti-D IgG preparations and unreactive with the pooled IgG from healthy individuals without detectable anti-D are isolated, grown, and the phage sequenced. Synthetic peptides are prepared and their ability to inhibit the hemolytic capacity of commercially prepared human polyclonal anti-D (Rhogam, Johnson and Johnson) is determined. Binding constants are also determined.

The instant invention is shown and described herein in what is considered to be the most practical, and preferred embodiments. It is recognized, however, that departures may be made therefrom which are within the scope of the invention, and that obvious modifications will occur to one skilled in the art upon reading this disclosure.

What is claimed is:

1. A method of obtaining peptide molecules which selectively bind to antibodies uniquely associated with a disease of a patient infected with a pathogenic bacterium or virus, comprising:

(a) isolating antibodies from the serum of a first patient having antibodies uniquely associated with the disease;

(b) binding the antibodies to a support surface;

(c) contacting the antibodies on the support surface with a library of peptide molecules in a manner so as to allow peptide molecules in the library to bind to the antibodies;

(d) obtaining peptide molecules in step (c) which bind to an antibody from the first patient;

(e) isolating antibodies from the serum of a second patient having antibodies uniquely associated with the same disease as the first patient;

(f) labeling the antibodies from the second patient with a detectable label;

(g) contacting the labeled antibodies of step (f) with the peptide molecules of step (d) in a manner so as to allow binding of the labeled antibodies to the molecules of step (d); and (h) obtaining peptide molecules which bind to antibodies of the first patient and to antibodies of the second patient.

2. The method of claim 1, further comprising:

(i) isolating antibodies from the serum of a third patient having antibodies uniquely associated with the same disease as the first patient;

(j) labeling the antibodies from the third patient with a detectable label;

(k) contacting the labeled antibodies of step (j) with the peptide molecules of step (h) in a manner so as to allow binding of the labeled antibodies to the peptide molecules of step (j); and (l) obtaining peptide molecules which bind to antibodies of the first, second and third patient.

3. The method of claim 2, further comprising:

(m) isolating antibodies from the serum of an additional patient having antibodies uniquely associated with the same disease as the first patient wherein the additional patient is different from the first patient, the second patient, and the third patient;

(n) labelling the antibodies from the additional patient with a detectable label;

(o) contacting the labelled antibodies of the additional patient with the peptide molecules of step (l) in a manner so as to allow binding of the labelled antibodies to the peptide molecules of step (l); and (p) obtaining peptide molecules which bind to antibodies of the first patient, second patient, third patient, and additional patient.

4. The method of claim 3, further comprising:

(q) repeating steps (m)–(p) a plurality of times thereby obtaining peptide molecules which bind to disease specific antibodies which antibodies are specific to the disease of the first patient, second patient, third patient, and each additional patient.

5. The method of claim 1, further comprising:

isolating the peptide molecules of step (h).

6. The method of claim 5, further comprising:

identifying the isolated peptide molecules.

7. The method of claim 1, further comprising:

obtaining peptide molecules which bind to disease specific antibodies which antibodies are specific to the disease of the first patient and the second patient by observing antibodies which bind to the peptide molecules of step (h).

8. The method of claim 1, further comprising:

repeating step (c) under more stringent binding conditions in order to determine antibodies with a higher binding affinity for the library of peptide molecules than the antibodies determined by carrying out step (c) a first time.

9. The method of claim 1, wherein the antibodies of step (f) are labelled with a label selected from the group consisting of a radioactive label, biotin, and fluorescein.

10. The method of claim 1, wherein the disease is caused by a virus selected from the group consisting of HIV, HCV and HBV.

11. The method of claim 1, where the support surface is the surface of polystyrene beads.

12. The method of claim 1, wherein the library of peptides is a library produced on the surface of a bacteriophage.

13. The method of claim 12, wherein the library of peptides contains more than 400 different bacteriophage with each having on its surface a peptide with a distinct, unique and different amino acid sequence.

14. The method of claim 13, wherein the library of peptides contains more than 8,000 different bacteriophage with each having on its surface a peptide with a distinct, unique and different amino acid sequence.

15. The method of claim 14, wherein the library of peptides contains more than 160,000 different bacteriophage with each having on its surface a distinct, unique and different amino acid sequence.

16. The method of claim 15, wherein the library of peptides contains more than 3,200,000 different bacteriophage with each having on its surface a distinct, unique and different amino acid sequence.

17. The method of claim 16, wherein the library of peptides contains more than 64,000,000 different bacteriophage with each having on its surface a distinct, unique and different amino acid sequence.

18. The method of claim 1, wherein the library of peptides is a library of peptides on the surface of bacteria.

19. A method of obtaining peptides which selectively bind to an antibodies uniquely associated with a disease of a patient infected with a pathogenic bacterium or virus, comprising:

(a) isolating antibodies from the serum of a first patient having antibodies uniquely associated with the disease;

(b) binding the antibodies to a support surface;

(c) contacting the antibodies on the support surface with a library of peptides expressed on bacteriophage in a manner so as to allow peptides to bind to the antibodies;

(d) obtaining the peptides expressed on bacteriophage in step (c) which bind to antibodies from the first patient;

(e) diluting the bacteriophage of step (d) and contacting the diluted bacteriophage with bacteria under conditions which allow the bacteriophage to infect the bacteria, reproduce and produce plaques;

(f) isolating antibodies from the serum of a second patient having antibodies uniquely associated with the same disease as the first patient;

(g) labeling the antibodies from the second patient having antibodies uniquely associated with a detectable label;

(h) contacting the labeled antibodies of step (g) with the plaques of step (e) in a manner so as to allow binding of the labeled antibodies to the plaques; and (i) obtaining peptides on the bacteriophage in the plaques which bind to antibodies of the first patient and to antibodies of the second patient and isolating these peptides.

20. A method of obtaining antibodies uniquely associated with a disease of a patient infected with a pathogenic bacterium or virus, comprising:

(a) isolating antibodies from the serum of a first patient having antibodies uniquely associated with the disease;

(b) binding the antibodies to a support surface;

(c) contacting the antibodies on the support surface with a library of peptides expressed on bacteriophage in a manner so as to allow peptides to bind to the antibodies;

(d) obtaining the peptides expressed on bacteriophage in step (c) which bind to an antibody from the first patient;

(e) diluting the bacteriophage of step (d) and contacting the diluted bacteriophage with bacteria under conditions which allow the bacteriophage to infect the bacteria, reproduce and produce plaques;

(f) isolating antibodies from the serum of a second patient having antibodies uniquely associated with the same disease as the first patient;

(g) labeling the antibodies from the second patient with a detectable label;

(h) contacting the labeled antibodies of step (g) with the plaques of step (e) in a manner so as to allow binding of the labeled antibodies to the plaques; and (i) obtaining antibodies of the second patient which bind to the same peptides as the antibodies of the first patient and isolating those antibodies.

* * * * *